US010070980B2

(12) United States Patent
Babkes et al.

(10) Patent No.: US 10,070,980 B2
(45) Date of Patent: Sep. 11, 2018

(54) ANCHORED NON-PIERCING DUODENAL SLEEVE AND DELIVERY SYSTEMS

(71) Applicant: Apollo Endosurgery, Inc., Austin, TX (US)

(72) Inventors: Mitchell H. Babkes, Santa Clarita, CA (US); Zachary P. Dominguez, Santa Barbara, CA (US); Christopher S. Mudd, Ventura, CA (US)

(73) Assignee: APOLLO ENDOSURGERY US, INC., Austin, TX (US)

( * ) Notice: Subject to any disclaimer, the term of this patent is extended or adjusted under 35 U.S.C. 154(b) by 348 days.

(21) Appl. No.: 13/921,082

(22) Filed: Jun. 18, 2013

(65) Prior Publication Data

US 2013/0281911 A1   Oct. 24, 2013

Related U.S. Application Data

(63) Continuation of application No. 13/276,208, filed on Oct. 18, 2011, now abandoned.
(Continued)

(51) Int. Cl.
*A61B 17/03* (2006.01)
*A61B 17/04* (2006.01)
*A61F 5/00* (2006.01)

(52) U.S. Cl.
CPC .......... *A61F 5/0079* (2013.01); *A61F 5/0076* (2013.01)

(58) Field of Classification Search
CPC .................................................. A61F 5/0079
See application file for complete search history.

(56) References Cited

U.S. PATENT DOCUMENTS

| 1,702,974 A | 2/1929 | MacDonald |
| 2,087,604 A | 7/1937 | Mosher |

(Continued)

FOREIGN PATENT DOCUMENTS

| CN | 1250382 A | 4/2000 |
| CN | 1367670 A | 9/2002 |

(Continued)

OTHER PUBLICATIONS

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.
(Continued)

*Primary Examiner* — Tatyana Zalukaeva
*Assistant Examiner* — Sara Sass
(74) *Attorney, Agent, or Firm* — Donald K. Jones

(57) ABSTRACT

An intragastric implant for obesity treatment is disclosed. The device delays digestion by providing a duodenal sleeve, and may also slows gastric emptying by limiting flow through the pyloric sphincter. The implant includes an elongated axially-compressible duodenal sleeve having a non-tissue-piercing anchor on a proximal end sized to lodge within the duodenal bulb. The anchor may have oppositely-directed anchoring flanges to resists migration in both directions. The sleeve may also have barbed ribs to resist proximal movement back up into the stomach. A method of implant includes collapsing/compressing the device and transorally advancing it through the esophagus to be deployed within the duodenum. A dissolvable jacket may constrain the implant for delivery and naturally dissolve upon implant. Removal of the implant may occur in the reverse.

8 Claims, 10 Drawing Sheets

Related U.S. Application Data

(60) Provisional application No. 61/479,714, filed on Apr. 27, 2011, provisional application No. 61/485,009, filed on May 11, 2011, provisional application No. 61/394,592, filed on Oct. 19, 2010.

(56) References Cited

U.S. PATENT DOCUMENTS

| | | | |
|---|---|---|---|
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | De |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | Garza |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0040804 A1* | 2/2003 | Stack ............. A61F 2/04 623/23.7 |
| 2003/0045896 A1 | 3/2003 | Murphy |
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1 | 6/2003 | Geitz |
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1* | 5/2004 | Kagan ............. A61F 2/04 604/264 |
| 2004/0117031 A1 | 6/2004 | Stack |
| 2004/0122452 A1 | 6/2004 | Deem |
| 2004/0122453 A1 | 6/2004 | Deem |
| 2004/0143342 A1 | 7/2004 | Stack |
| 2004/0148034 A1 | 7/2004 | Kagan |

(56) References Cited

U.S. PATENT DOCUMENTS

| | | |
|---|---|---|
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann |
| 2005/0055039 A1* | 3/2005 | Burnett ............. A61B 5/14539 606/151 |
| 2005/0085923 A1 | 4/2005 | Levine |
| 2005/0096692 A1 | 5/2005 | Linder |
| 2005/0110280 A1 | 5/2005 | Guy |
| 2005/0131485 A1 | 6/2005 | Knudson |
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1 | 11/2005 | Roth |
| 2005/0256587 A1* | 11/2005 | Egan .................... A61F 5/0076 623/23.65 |
| 2005/0261711 A1 | 11/2005 | Okada |
| 2005/0267595 A1 | 12/2005 | Chen |
| 2005/0267596 A1 | 12/2005 | Chen |
| 2005/0273060 A1* | 12/2005 | Levy et al. .................... 604/192 |
| 2005/0277975 A1 | 12/2005 | Saadat |
| 2006/0020247 A1* | 1/2006 | Kagan ............. A61B 17/00234 604/264 |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo |
| 2007/0010864 A1 | 1/2007 | Dann |
| 2007/0016262 A1 | 1/2007 | Gross |
| 2007/0021761 A1 | 1/2007 | Phillips |
| 2007/0078476 A1 | 4/2007 | Hull |
| 2007/0083224 A1 | 4/2007 | Hively |
| 2007/0100368 A1 | 5/2007 | Quijano |
| 2007/0118168 A1 | 5/2007 | Lointier |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk |
| 2007/0185374 A1 | 8/2007 | Kick |
| 2007/0185375 A1 | 8/2007 | Kick |
| 2007/0239284 A1 | 10/2007 | Skerven |
| 2007/0250020 A1 | 10/2007 | Kim |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker |
| 2008/0015618 A1 | 1/2008 | Sonnenschein |
| 2008/0058840 A1 | 3/2008 | Albrecht |
| 2008/0058887 A1 | 3/2008 | Griffin |
| 2008/0065122 A1 | 3/2008 | Stack |
| 2008/0071305 A1 | 3/2008 | DeLegge |
| 2008/0097513 A1 | 4/2008 | Kaji |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner |
| 2008/0221595 A1 | 9/2008 | Surti |
| 2008/0228205 A1 | 9/2008 | Sharkey |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0249635 A1 | 10/2008 | Weitzner |
| 2008/0255601 A1 | 10/2008 | Birk |
| 2008/0255678 A1 | 10/2008 | Cully |
| 2008/0262529 A1 | 10/2008 | Jacques |
| 2008/0306506 A1 | 12/2008 | Leatherman |
| 2009/0012553 A1 | 1/2009 | Swain |
| 2009/0082644 A1 | 3/2009 | Li |
| 2009/0093767 A1 | 4/2009 | Kelleher |
| 2009/0093837 A1 | 4/2009 | Dillon |
| 2009/0131968 A1 | 5/2009 | Birk |
| 2009/0132031 A1 | 5/2009 | Cook |
| 2009/0149879 A1 | 6/2009 | Dillon |
| 2009/0177215 A1 | 7/2009 | Stack |
| 2009/0198210 A1 | 8/2009 | Burnett |
| 2009/0216337 A1 | 8/2009 | Egan |
| 2009/0259246 A1 | 10/2009 | Eskaros |
| 2009/0275973 A1 | 11/2009 | Chen |
| 2009/0287231 A1 | 11/2009 | Brooks |
| 2009/0299327 A1 | 12/2009 | Tilson |
| 2009/0299486 A1 | 12/2009 | Shohat |
| 2009/0312597 A1 | 12/2009 | Bar |
| 2010/0030017 A1 | 2/2010 | Baker |
| 2010/0049224 A1 | 2/2010 | Vargas |
| 2010/0081991 A1 | 4/2010 | Swisher |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans |
| 2010/0121371 A1 | 5/2010 | Brooks |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe |
| 2010/0256776 A1 | 10/2010 | Levine |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes |
| 2010/0331756 A1 | 12/2010 | Meade |
| 2010/0332000 A1 | 12/2010 | Forsell |
| 2011/0004236 A1* | 1/2011 | Priplata ............. A61B 17/3468 606/192 |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |

FOREIGN PATENT DOCUMENTS

| | | |
|---|---|---|
| DE | 8804765 U1 | 5/1989 |
| DE | 102007025312 A1 | 11/2008 |
| EP | 1396242 A1 | 3/2004 |
| EP | 1396243 A1 | 3/2004 |
| EP | 1397998 A1 | 3/2004 |
| EP | 1774929 A2 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 A1 | 4/2007 |
| FR | 2941617 A1 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 A1 | 1/1988 |
| WO | 1988000027 | 1/1988 |
| WO | 0015158 A1 | 3/2000 |
| WO | 2000032092 | 6/2000 |
| WO | 0110359 A1 | 2/2001 |
| WO | 0149245 A2 | 7/2001 |
| WO | 0166166 A2 | 9/2001 |

(56) References Cited

FOREIGN PATENT DOCUMENTS

| | | |
|---|---|---|
| WO | 0235980 A2 | 5/2002 |
| WO | 03055419 A1 | 7/2003 |
| WO | 03105732 A1 | 12/2003 |
| WO | 2004019671 A2 | 3/2004 |
| WO | 2005007231 A1 | 1/2005 |
| WO | 2005094257 A2 | 10/2005 |
| WO | 2005097012 | 10/2005 |
| WO | 2005097012 A2 | 10/2005 |
| WO | 2005110280 | 11/2005 |
| WO | 2005110280 A2 | 11/2005 |
| WO | 2006044640 A1 | 4/2006 |
| WO | 2006020370 | 6/2006 |
| WO | 2006063593 A2 | 6/2006 |
| WO | 2006090018 A1 | 8/2006 |
| WO | 2006111961 A2 | 10/2006 |
| WO | 2006118744 A1 | 11/2006 |
| WO | 2007027812 A2 | 3/2007 |
| WO | 2007053556 A1 | 5/2007 |
| WO | 2007076021 A2 | 7/2007 |
| WO | 2007092390 A2 | 8/2007 |
| WO | 2007110866 A2 | 10/2007 |
| WO | 2008101048 A2 | 8/2008 |
| WO | 2008112894 A1 | 9/2008 |
| WO | 2008132745 A2 | 11/2008 |
| WO | 2010042062 A1 | 4/2010 |
| WO | 2010074712 | 7/2010 |
| WO | 2010074712 A2 | 7/2010 |
| WO | 2010087757 A1 | 8/2010 |
| WO | 2010117641 A2 | 10/2010 |

OTHER PUBLICATIONS

Baggio et al. 'Biology of Integrins: GLP-1 and GIP'; Gastroenrology; V. 132; pp. 2131-2157; 2007.
Berne et al; 'Physiology'; V. 5; pp. 55-57, 210, 428, 540, 554, 579, 584, 591; 2004.
Boulant et al.; 'Cholecystokinin in Transient Lower Oesophageal Sphincter Relation Due to Gastric Distension in Humans'; Gut; V. 40; pp. 575-581; 1997.
Bradjewin et al; 'Dose Ranging Study of the Effects of Cholecystokinin in Healthy Volunteers'; J. Psychiatr. Neurosci.; V. 16 (2); pp. 91-95; 1991.
Chaudhri; 'Can Gut Hormones Control Appetite and Prevent Obesity?' Diabetes Care; V. 31; Supp 2; pp. S284-S289; Feb. 2008.
Cohen et al.; 'Oxyntomodulin Suppresses Appetite and Reduces Food in Humans'; J. Clin. Endocrinol. Metab.; V. 88; pp. 4696-4701; 2003.
Dakin et al.; 'Oxyntomodulin Inhibits Food Intake in the Rat'; Endocrinology; V. 142; pp. 4244-4250; 2001.
Dakin et al.; 'Peripheral Oxyntomodulin Reduces Food Intake and Body Weight gain in Rats'; Endocrinology; V. 145; No. 6; pp. 2687-2695; Jun. 2004.
Davison; 'Activation of Vagal-Gastric Mechanoreceptors by Cholecystokinin'; Proc. West. Pharmocol. Soc; V. 29; pp. 363-366; 1986.
Ekblad et al.; 'Distribution of Pancreatic Peptide and Peptide-YY'; Peptides; V. 23; pp. 251-261;2002.
Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Houpt; 'Gastrointestinal Factors in Hunger and Satiety'; Neurosci. And Behav. Rev.; V. 6; pp. 145-164; 1982.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Naslund et al.; 'Prandial Subcutaneous Injection of Glucagon-Like Peptide'; Br. J. Nutr.; V. 91; pp. 439-446; 2004.
Renshaw et al. 'Peptide YY: A Potential Therapy for Obesity'; Current Drug Targets; V. 6; pp. 171-179; 2005.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.
BIB Bioenterics Intragastric Balloon Program, 'Take Control of Your Weight and Your Life/The Solution for You,' Inamed Health, pp. 1-2; Jan. 19, 2004.
BIB Bioenterics Intragastric Balloon Program, 'Taking the Next Step/Take Control of Your Weight and Your Life,' Inamed Health, pp. 1-9; Apr. 29, 2004.
BIB Data Sheet Directions for Use, 'BioEnterics Intragastric Balloon System,' Inamed Health, 1-12 pp.
'Living With the Bib/BioEnterics Intragastric Balloon Program,' Inamed Health; 1-10 Patient Information Brochure; pp.; May 1, 2005.

* cited by examiner

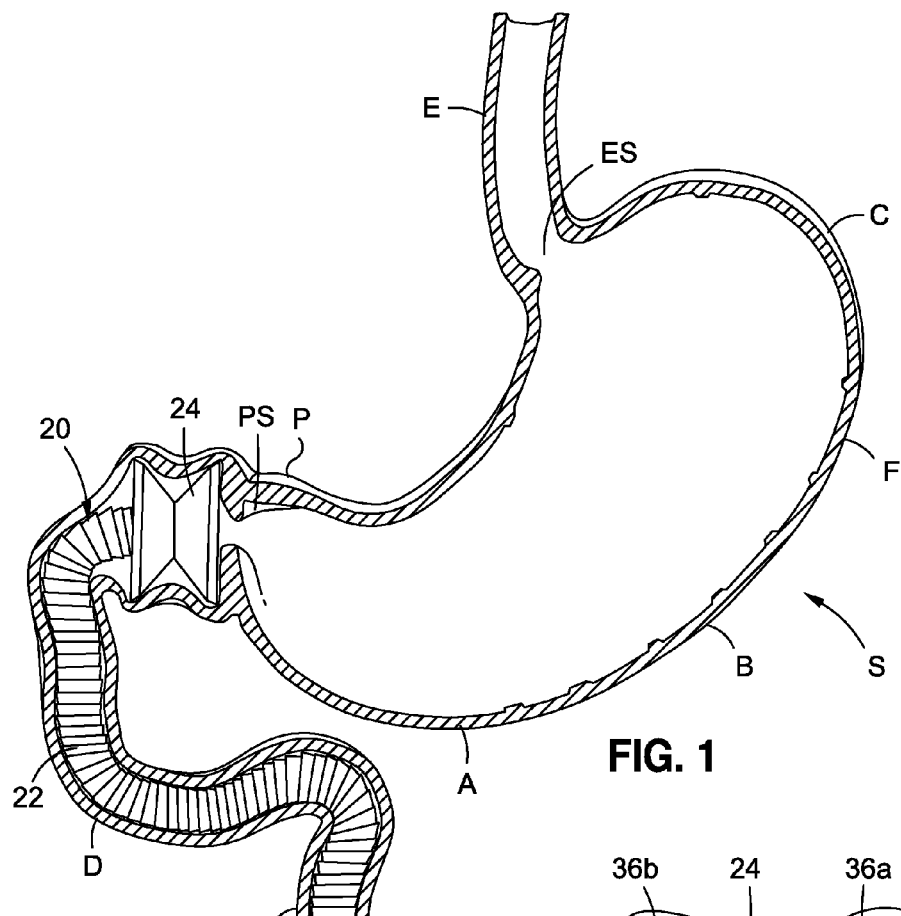

ANCHORED NON-PIERCING DUODENAL SLEEVE AND DELIVERY SYSTEMS

RELATED APPLICATIONS

The present application is a continuation of U.S. patent application Ser. No. 13/276,208, filed Oct. 18, 2011, which claims priority to U.S. Provisional Application No. 61/479,714, filed Apr. 27, 2011; U.S. Provisional Application No. 61/485,009, filed May 11, 2011; and U.S. Provisional Application No. 61/394,592, filed Oct. 19, 2010, the disclosures of which are incorporated by reference herein.

FIELD OF THE INVENTION

The present invention is directed to intragastric devices used for the treatment of obesity, and in particular to duodenal sleeves having a non-piercing anchor and delivery systems therefor.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States is projected to reach approximately 400,000 annually in 2010.

Examples of surgical methods and devices used to treat obesity include the LAP-BAND® (Allergan, Inc., Irvine, Calif.) gastric band and the LAP-BAND AP® (Allergan, Inc., Irvine, Calif.). However, surgery might not be an option for every obese individual; for certain patients, non-surgical therapies or minimal-surgery options are more effective or appropriate.

Intragastric balloons are also well known in the art as a means for treating obesity. One such inflatable intragastric balloon is described in U.S. Pat. No. 5,084,061 and is commercially available as the BioEnterics Intragastric Balloon System (sold under the trademark BIB® System). These devices are designed to provide therapy for moderately obese individuals who need to shed pounds in preparation for surgery, or as part of a dietary or behavioral modification program. The BIB System, for example, consists of a silicone elastomer intragastric balloon that is inserted into the stomach in an empty or deflated state and thereafter filled (fully or partially) with a suitable fluid. The balloon occupies space in the stomach, thereby leaving less room for food and creating a feeling of satiety for the patient.

Another type of surgical device for treating obesity is a duodenal sleeve, which is a flexible tube endoscopically placed in and along the duodenum, which is located at the beginning of the intestinal tract, to slow down or interrupt the digestive process which occurs there. Examples of such devices include those shown in U.S. Pat. No. 5,820,584 to Crabb and U.S. Pat. No. 7,476,256 to Meade, et al. Duodenal sleeves require some sort of anchor to prevent migration down the intestinal tract, typically utilizing a metallic stent with barbs as in the Meade patent and as described in "First human experience with endoscopically delivered and retrieved duodenal-jejunal bypass sleeve," Rodriguez-Grunert, et al., *Surgery for Obesity and Related Diseases*, 4:57-59 (2008).

Despite many advances in the design of intragastric obesity treatment devices, there remains a need for an improved duodenal sleeve that can be implanted for longer periods than before or otherwise address certain drawbacks of previous devices.

SUMMARY OF THE INVENTION

The present invention addresses the above-described problems by providing a transorally inserted, intragastric device for the treatment of obesity. The device includes a sleeve for placement in the duodenum having a tubular body with proximal and distal ends. A radially collapsible anchor surrounds the proximal end of the tubular body, the anchor having an expanded state that can act to prevent passage of the device through the pyloric sphincter. The anchor further includes two conical flanges concentrically-disposed around the tubular body and angled away from one another so as to impede movement of the anchor within the duodenum in both a proximal direction and in a distal direction. The device is formed of a material that will resist structural degradation over a period of at least six months within the gastrointestinal tract. Preferably, the sleeve is axially collapsible/expandable and includes exterior ribs to resist movement within the duodenum in one direction. The exterior ribs on the sleeve may be conical and extend the length of the sleeve and angle in the proximal direction to resist movement within the duodenum in the proximal direction. In one embodiment, the conical ribs are shaped to nest within one another for axial collapse of the sleeve. In a particularly preferred form, the anchor surrounding the proximal end of the tubular body has no metal component.

Another aspect of the present application is a transorally inserted, intragastric device for the treatment of obesity. The device has a stomach anchoring member with a collapsed, delivery size, and an expanded, deployed size larger than a pyloric sphincter, the stomach anchoring member having no tissue-piercing elements. A duodenal anchoring member has a collapsed, delivery size, and an expanded, deployed size larger than a pyloric sphincter, the duodenal anchoring member also has no tissue-piercing elements. Further, an elongated duodenal sleeve for placement in the duodenum has a tubular body with proximal and distal ends, the proximal end extending to the stomach anchoring member on the stomach side of the pyloric sphincter and forming a compressible channel through the pyloric sphincter. Finally, a plurality of cords extends the length of the device from the stomach anchoring member to the distal end of the duodenal sleeve. The device is formed of a material that will resist structural degradation over a period of at least six months within the gastrointestinal tract.

In the preceding intragastric device, the anchoring member may comprise a funnel-shaped structure that extends into the stomach, wherein the duodenal sleeve continues and widens in a proximal direction along the funnel-shaped structure. The stomach anchoring member may be formed by a plurality of resilient rings sufficiently compressible to be delivered transorally, and sufficiently large to spring outward to form the funnel-shaped structure in contact with the antrum area of the stomach. The duodenal anchoring member may also be formed by resilient rings sufficiently compressible to be delivered transorally, and sufficiently large to spring outward into contact with a duodenal bulb area of the duodenum. In one embodiment, the plurality of resilient rings are differently sized and having a central larger ring such that the duodenal sleeve has a bulge in the area of the duodenal anchoring member. The device further may include a plurality of spaced resilient rings along the duodenal sleeve and connected to the cords for anti-migration/anti-kinking characteristics. Also, the device may have a flexible annular membrane spanning the stomach anchoring member and having a central through hole that defines the flow orifice from the stomach into the duodenal sleeve. Preferably, a plurality of grasping tabs project proximally from the stomach anchoring member, and the tabs may be proximal ends of the cords.

Another transorally inserted, intragastric device for the treatment of obesity comprises a stomach anchoring member with at least one resilient ring sufficiently compressible to be delivered transorally and sufficiently large to spring outward into contact with the lower stomach adjacent the pyloric sphincter. A duodenal anchoring member has a plurality of resilient rings sufficiently compressible to be delivered transorally, and sufficiently large to spring outward into contact with a duodenal bulb area of the duodenum. In addition, an elongated duodenal sleeve for placement in the duodenum has a tubular body with proximal and distal ends, the proximal end extending to the stomach anchoring member on the stomach side of the pyloric sphincter, and forming a compressible channel through the pyloric sphincter. Again, the device resists structural degradation over at least six months within the gastrointestinal tract.

The stomach anchoring member may be a funnel-shaped structure that extends into the stomach, wherein the duodenal sleeve continues and widens in a proximal direction along the funnel-shaped structure. In one embodiment, the stomach anchoring member comprises a plurality of the resilient rings forming a funnel-shaped structure in contact with the antrum area of the stomach. The device may have a flexible annular membrane spanning the resilient ring of the stomach anchoring member and having a central through hole that defines the flow orifice from the stomach into the duodenal sleeve. In the embodiment where the stomach anchoring member comprises a plurality of the resilient rings sized progressively larger in the proximal direction to form a funnel-shaped structure that extends into the stomach, the flexible annular membrane spans the resilient ring closest to the duodenal anchoring member. A plurality of grasping tabs may project proximally from the stomach anchoring member, and the grasping tabs desirably comprise proximal ends of the cords. The plurality of resilient rings of the duodenal anchoring member preferably spring outward into contact with a duodenal bulb area of the duodenum and are differently sized, having a central larger ring such that the duodenal sleeve has a bulge in the area of the duodenal anchoring member. The device preferably includes a plurality of spaced resilient rings along the duodenal sleeve and connected to the cords for anti- for migration/anti-kinking characteristics.

A still further passive intragastric obesity treatment implant disclosed herein comprises an umbrella member having expanded diameter sufficient to prevent passage through the pyloric sphincter, the umbrella member being formed of a plurality of longitudinal struts. A duodenal anchor connects to one end of the umbrella member, the duodenal anchor having a size that permits it to pass through the pyloric sphincter and be formed of a material of sufficient mass and specific gravity that prevents it from migrating back up through the pyloric sphincter. The implant is formed of a material which permits it to be compressed into a substantially linear delivery configuration and that will resist degradation over a period of at least six months within the stomach.

Another aspect of the application is a transorally inserted, intragastric device for the treatment of obesity comprising a sleeve for placement in the duodenum having an axially collapsible tubular body with proximal and distal ends. A radially collapsible anchor surrounds the proximal end of the tubular body and has a radially expanded state that prevents passage through the pyloric sphincter. The anchor including exterior features to resist movement within the duodenum in both proximal and distal directions. The device is formed of a polymeric material absent of any metal that will resist structural degradation over a period of at least six months within the gastrointestinal tract. Preferably, the sleeve includes exterior ribs to resist movement within the duodenum in one direction. The exterior ribs on the sleeve may be conical and extend the length of the sleeve and angle in the proximal direction to resist movement within the duodenum in the proximal direction. In one embodiment, the conical ribs are shaped to nest within one another for axial collapse of the sleeve. In a particularly preferred form, the anchor surrounding the proximal end of the tubular body has no metal component. The exterior features on the anchor may be two conical flanges concentrically-disposed around the tubular body and angled away from one another.

A further aspect disclosed herein is a transorally inserted, intragastric system for the treatment of obesity. The system has an implant with a sleeve for placement in the duodenum having an axially collapsible tubular body with proximal and distal ends. A radially collapsible anchor surrounding the proximal end of the tubular body has a radially expanded state that prevents passage through the pyloric sphincter. The implant is formed of a material that will resist structural degradation over a period of at least six months within the gastrointestinal tract. Finally, a jacket is sized to surround and retain the implant in its collapsed configuration, the jacket being easily removable from around the implant. Preferably, the sleeve includes exterior ribs to resist movement within the duodenum in one direction.

Desirably, the exterior ribs on the sleeve may be conical and extend the length of the sleeve and angle in the proximal direction to resist movement within the duodenum in the proximal direction. In one embodiment, the conical ribs are shaped to nest within one another for axial collapse of the sleeve. In a particularly preferred form, the anchor surrounding the proximal end of the tubular body has no metal component. The anchor may include two conical flanges concentrically-disposed around the tubular body and angled away from one another so as to resist movement of the anchor within the duodenum in both proximal and distal directions. Preferably, the anchor surrounding the proximal end of the tubular body has no metal component. The jacket may have a rounded closed distal end, and an open proximal end. The jacket may be dissolvable. The jacket preferably has a first length surrounding the sleeve and a second length surrounding the anchor which is stronger than the first length.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 1 is a sectional view through a human stomach illustrating an exemplary intragastric obesity treatment implant having a duodenal sleeve deployed in the duodenum and a dual-flanged anchor positioned in the duodenal bulb area, just distal to the pyloric sphincter;

FIG. 2 is a close up view of the duodenal bulb area with the intragastric obesity treatment implant expanded to its as-molded shape;

FIG. 13 illustrates another intragastric device implanted in the stomach spanning the pyloric sphincter and having a duodenal sleeve, while

DETAILED DESCRIPTION OF THE PREFERRED EMBODIMENTS

Figure 3A:
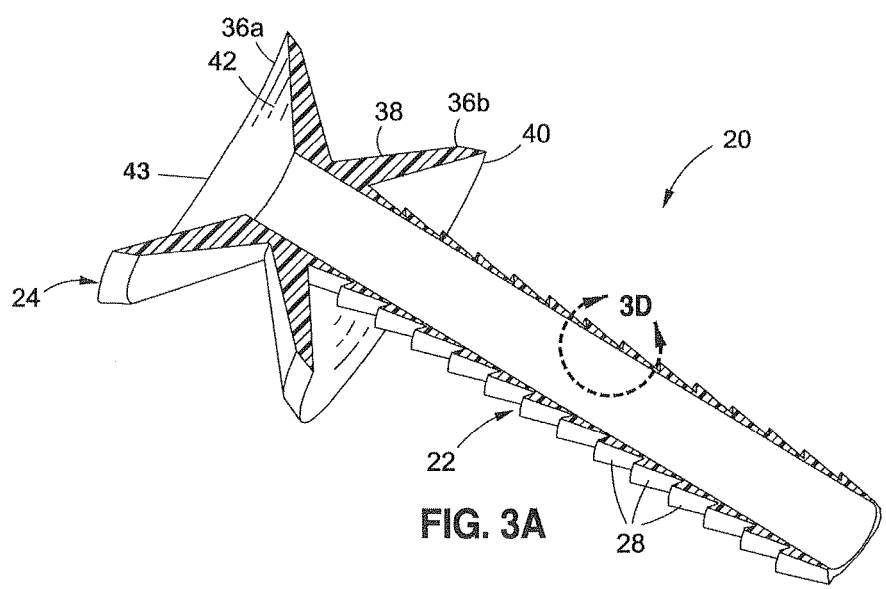
FIGS. 3A-3D show the proximal end of the expanded intragastric obesity treatment implant in its as-molded shape to help visualize the device.
Figure 3B:
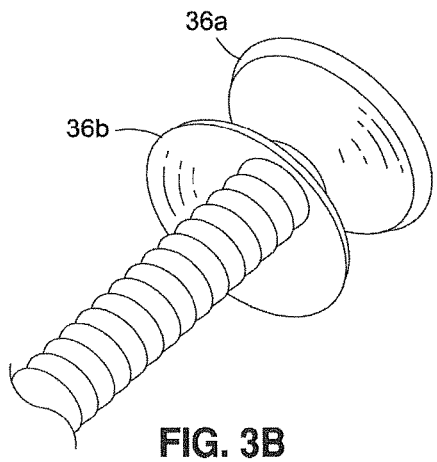
Figure 3C:
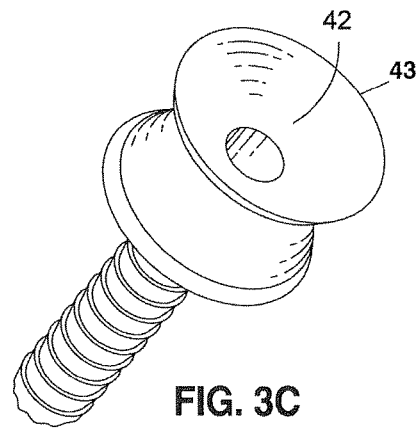
Figure 3D:
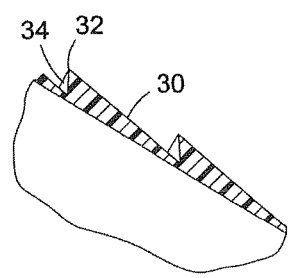

The present invention is directed to intragastric devices for passively treating obesity by limiting nutrient absorption/caloric assimilation. Furthermore, the exemplary device described herein may affect the rate of stomach emptying. The term "passive" refers primarily to a lack of any moving parts within the devices, but in general to the inert nature of the various devices.

FIG. 1 illustrates an exemplary intragastric obesity treatment implant 20, but also illustrates the anatomy of the human stomach, which will be described first. The major function of the stomach S is to temporarily store food and release it slowly into the duodenum D. The esophagus E extending downward from the mouth connects to the stomach via esophageal sphincter ES, which regulates flow food into the stomach cavity. The cardia C surrounds the superior opening of the stomach. The rounded portion superior to the body B and adjacent the cardia is the fundus F. Inferior to the fundus is the large central portion of the stomach, called the body that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum A connects the body to the pyloris P, which leads into the duodenum. Below the stomach, the duodenum leads into the upper part of the small intestine (not shown); the jejunum J makes up about one-third of the small intestine. The region of the stomach that connects to the duodenum is the pylorus. The pylorus communicates with the duodenum of the small intestine via the pyloric sphincter PS (valve). This valve regulates the passage of chyme from stomach to duodenum and it prevents backflow of chyme from duodenum to stomach.

FIG. 1 illustrates the exemplary intragastric obesity treatment implant 20 having a duodenal sleeve 22 deployed in the duodenum and a dual-flanged anchor 24 positioned in the duodenal bulb area, just distal to the pyloric sphincter PS. This application discloses a single use gastrointestinal (GI) implant that resides inside the duodenum D. It has been demonstrated that duodenal sleeves, as this device may be classified, limit food contact against the intestinal walls. It is known that most nutrient absorption occurs within the duodenum D. The device lines the duodenal walls, and possibly the jejunum J, and is anticipated to limit nutrient absorption/caloric assimilation, thereby inducing weight loss. More particularly, the duodenal sleeve 22 desirably lines (i.e. contacts) the upper duodenal wall, partially preventing nutrient absorption by inhibiting or delaying the point at which chyme from the stomach contacts the mucous membranes of the intestine.

The entire device is formed of a material that will resist structural degradation over a period of at least six months within the stomach. In this context, the term "structural degradation" means that the device will retain structural integrity sufficiently to perform its intended function for a desired time period, for example 6 months. In one sense, the device is nonbiodegradable for the desired time period, though some biodegradation may commence short of structural degradation. The anchor 24 is to be made of a compliant plastic material, and is desirably integrally molded with the rest of the device. The anchor is configured to gently expand against the walls of the duodenal bulb. The anchor and indeed the implant 20 has no metal pieces (i.e., is absent of any metal), which have sometimes been found to cause AE's, since metal has been seen to ulcerate GI tissues, especially when applying constant pressure. It is even possible that metal features can push through the duodenal walls, breaching the body's sterile barrier and causing death. As a result, no piercing of the stomach or intestinal walls is required to anchor this device, and it may be implanted in a minimally invasive manor, through the esophagus, without any surgical procedure. This device requires no tissue modifications, and may be removed at any time.

FIG. 2 is a close up view of the duodenal bulb area and intragastric obesity treatment implant 20 expanded to its as-molded shape. The term "as-molded shape" refers to the expanded shape of the implant 20 as it would appear after fabrication and in the absence of any surrounding constriction. It should be apparent to the reader that after expansion within the duodenum D the implant 20 expands until it contacts the surrounding duodenal walls, and as such is subject to a certain amount of constriction. However, the implant 20 is fabricated to have a size just slightly larger than the duodenum and duodenal bulb area, and as such can be viewed as expanding if not completely to, almost to its "as-molded shape." Stated a different way, the "as-molded shape" refers to the expanded shape of the implant 20 either in the absence of constriction or as implanted and shown in the drawings.

FIGS. 3A-3D show enlarged details of the proximal end of the intragastric obesity treatment implant 20 in its as-molded shape to help visualize the device. The duodenal sleeve 22 is substantially tubular with a smooth inner lumen 26 open on both ends and a rough or barbed outer surface. In a preferred embodiment, the outer surface features a series of evenly spaced fully circular barbed ribs 28 that protrude outwardly in the proximal direction from the thin walls of the sleeve. Specifically, each of the ribs 28 includes a relatively shallowly-angled conical distal surface 30 terminating at a circular tip 32 leading to a substantially more steeply-angled conical proximal surface 34. The ribs 28 extend in series along the length of the duodenal sleeve 22 from a distal end of the sleeve to the proximal dual-flanged anchor 24.

The series of ribs 28 serve three purposes. First, they provide circumferential stiffness to the sleeve 22, which is very thin and most flexible between each rib. Secondly, the "sharp", thin edges of the ribs are angled in a proximal direction, so as to grip the duodenal walls in a mode that is most prone to proximal movement. The series of ribs 28 thus provides a soft one-way anchor for the duodenal sleeve 22 that resists migration in a proximal direction, or toward the stomach, during routine digestive peristaltic action when implanted in the duodenum D. The third purpose of the ribs 28 is to "nest" together closely when the implant 20 in its collapsed/compressed state.

The material of the implant 20 desirably has elasticity so that the implant may be compressed both longitudinally (the sleeve 22) and radially (the anchor 24). As will be explained below, a constraint is placed on the implant 20 for transoral delivery down the esophagus E to the duodenum D. In a preferred embodiment, the constraint is released and the implant 20 spontaneously expands into contact with the surrounding duodenal walls. With respect to the duodenal sleeve 22, the expansion may alternatively be assisted by a device that contacts its distal end and is used to pull the distal end away from the proximal end (which may be anchored in the duodenal bulb or held by a proximal end of the delivery device) to stretch the sleeve. As such, the material and configuration of the sleeve 22 may be biased toward expansion without necessarily being capable of immediate self-expansion. An analogy for this is a ribbed straw for drinking which may be pulled or bent into an angle.

With reference back to FIGS. 3A-3D, the proximal end of the duodenal sleeve 22 forms a non-tissue-piercing anchoring portion 24 that seats inside the duodenal bulb and is intended to limit migration down the intestines, or back into the stomach. The soft dual-flanged anchor 24 has a conical proximal flange 36a angled in a proximal direction and a conical distal flange 36b connected at its base to the proximal flange angled in a distal direction. Both flanges 36a, 36b have "sharp" edges and thicker base legs. That is, the flanges taper from a wide base 38 to narrow circular edges 40. The oppositely angled proximal and distal flanges 36a, 36b help resist fore and aft movement of the implant 20. However, the absence of any metal and soft nature of the flange material prevents piercing of the surrounding duodenal wall and helps resist irritation.

The proximal anchor 24, and in particular the proximal conical flange 36a, forms an intake funnel 42 that leads to the lumen 26 of the duodenal sleeve 22. The intake funnel 42 has a proximal opening 43 at its largest diameter. The smallest diameter of the funnel 42, which preferably coincides with the constant diameter of the lumen 26, may be sized to reduce the volume flow rate exiting the stomach S through the pyloric sphincter PS. With reference to FIG. 2, the pyloric sphincter PS as shown in a contracted state, but regularly expands to permit boluses of chyme to pass therethrough. The funnel 42 and lumen 26 provide a maximum diameter passageway which may be designed to be smaller than the maximum expanded diameter of the pyloric sphincter PS. As such, the implant 20 thus may reduce the rate of stomach emptying, further contributing to weight loss.

Figure 4:
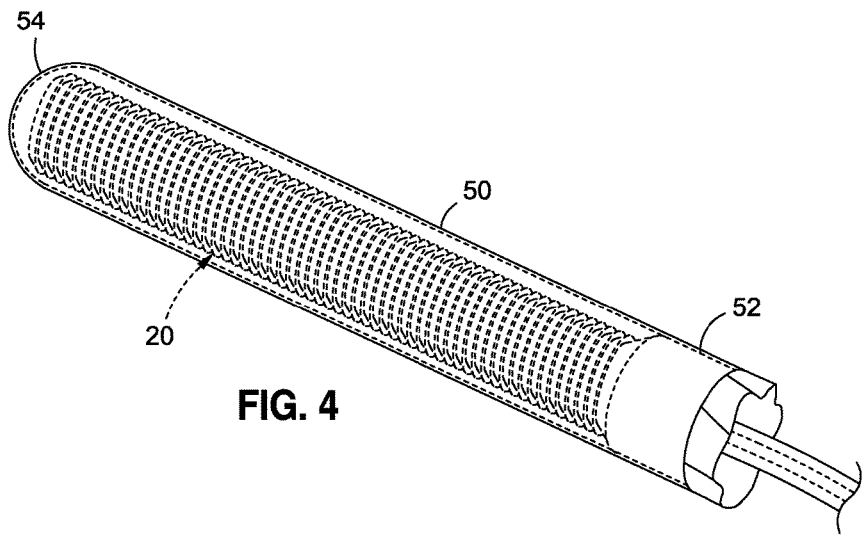
FIG. 4 illustrates the intragastric obesity treatment implant after removal from a shipping package in its collapsed/compressed state within a delivery jacket as it would look before inserting down the esophagus.
Figure 5:
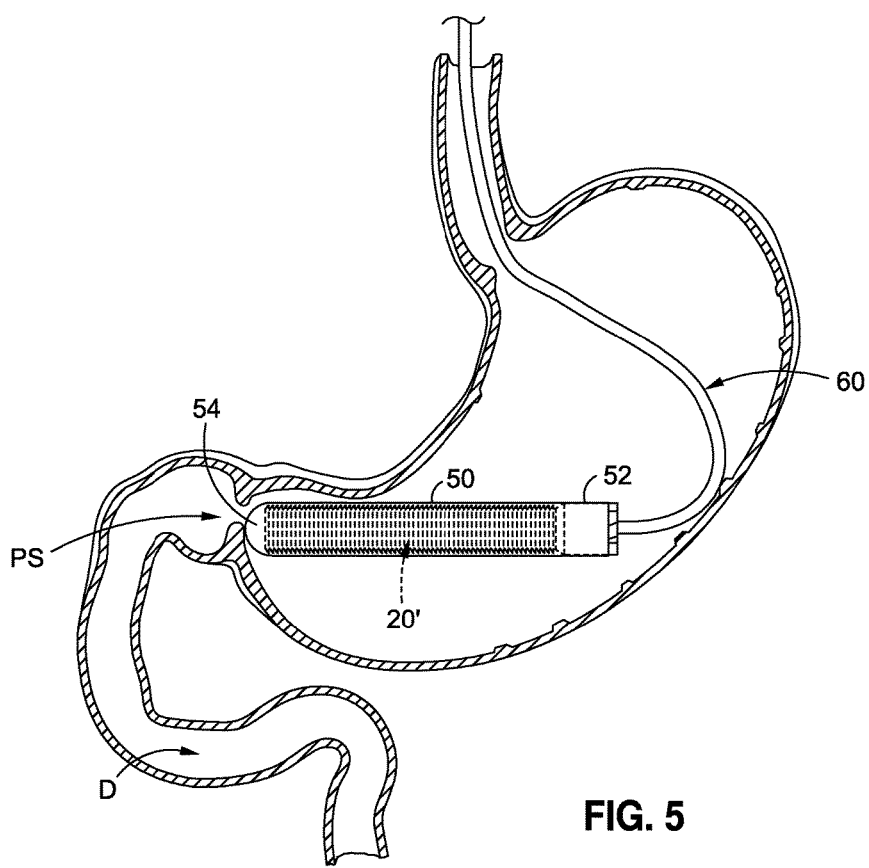
FIG. 5 shows the collapsed/compressed intragastric obesity treatment implant on the end of a flexible delivery member inserted down the esophagus and poised for advancement through the pyloric sphincter into an implant position.

FIG. 4 shows the exemplary intragastric obesity treatment implant 20' in a collapse/compressed state such as after removal from a shipping package, while FIG. 5 shows the collapsed/compressed implant 20 on the end of a flexible delivery member 60 inserted down the esophagus E and poised for advancement through the pyloric sphincter PS. The implant 20' is shown constrained by a delivery jacket 50 as it would look before inserting down the esophagus E. The delivery jacket 50 includes a proximal collar 52 which surrounds the proximal anchor 24 (not shown) may be formed with somewhat more strength than the jacket 50 to radially constrain the larger flanges 36a, 36b. Indeed, the jacket 50 may be sized so as to just axially collapse the duodenal sleeve 22, or it may also radially compress the sleeve. The jacket 50 is intended to constrain the sleeve 22 during delivery through the esophagus E, and thus a maximum delivery diameter may be derived from experience and depending on the patient which is suitable for only axially collapsing the sleeve. The jacket 50 is closed at a rounded distal end 54 to ease delivery through the winding esophagus, stomach, and duodenum. A lubricant may be used to facilitate this advancement.

In one particular configuration the delivery jacket 50 may be made of a gel that rapidly dissolves in the stomach environment. One example of a gel material suitable for the jacket 50 is the type of gel used for gel caps for ingestible pills. The dissolvable gel may be similar to caps used in pills for medicating large animals, and is completely inert to the human body. In the GI acid environment, the gel will dissolve rather quickly. Dissolution can even be accelerated to attain a pre-determined holding time by adding a series of holes through the gel wall, and varying their size, spacing, and number accordingly. However, a gel that better withstands the environment of the stomach and gastrointestinal tract for a short period is preferred. If the collapsed/compressed length of the implant 20 is such that the device remains partly in and partly out of the stomach, then a gel or other material that retains its integrity around the device during the delivery procedure is needed. For instance, a material that breaks down after about 5-10 minutes in the stomach would be appropriate.

In another configuration, the jacket 50 may not be dissolvable, but instead may be removed from around or pulled off the implant 20 when in position in the duodenum D. For instance, the flexible delivery member 60 may include a first portion that grasps the implant 20, and a second portion movable with respect to the first portion that can pull the jacket 50 in a proximal direction. The rounded distal end 54 may be tearable or dissolvable to facilitate removal of the jacket 50, or the distal end may be open with an elastic cincture to hold the sleeve 22 in a collapsed state. Furthermore, other ways to constrain the implant 20 are contemplated, including a more substantial overtube from which the implant is expelled and the like, as will be described below. The implant itself should not be considered limited to a particular delivery methodology.

In a typical procedure, the entire sleeve 22 may be accordion-compressed over the axially-stiff but laterally flexible installation/guide-tube 60. Before packaging, the device is fully compressed and held in its compressed state, while the delivery jacket 50 is placed over the distal end. The jacket 50 need not be closed on its proximal end. In this configuration, the device is ready for implantation.

Device delivery desirably occurs as follows: First, the compressed, gel-covered implant 20 would be routed down the esophagus by aid of its attached guide tube 60 or within a cannula device (not shown). The physician temporarily halts advancement of the implant 20 at the distal end of the stomach S, adjacent to the pylorus P. The implant 20 could be manufactured to include a radiopaque material such as Barium Sulphate for x-ray visualization at any present or future time. A fluoroscope would be utilized to visualize placement during the implantation procedure. No endoscope need be used. When located adjacent to the pylorus P, the physician pushes the implant 20 firmly through the pyloric sphincter PS, using the guide tube 60, and into the duodenal bulb. The implant 20 would then be held in that location until the gel jacket 50 begins to dissolve. Alternatively, the jacket 50 is removed from around the implant 20. The proximal dual-flange anchor 24 then immediately expands within the duodenal bulb, fixing the device in place, and thus limiting movement in either direction. Normal peristaltic action would then be relied on to fully deploy the sleeve "automatically", into its fully expanded state down the duodenum. Alternatively, as mentioned above, an obturator attached to the distal end of the sleeve 22 may be advanced to assist axial deployment thereof. The device is then left in place for a predetermined length of time, such as 6 months, while the patient is monitored for weight loss and any signs of malfunction.

Figures 6A, 6B, 6C, 6D:
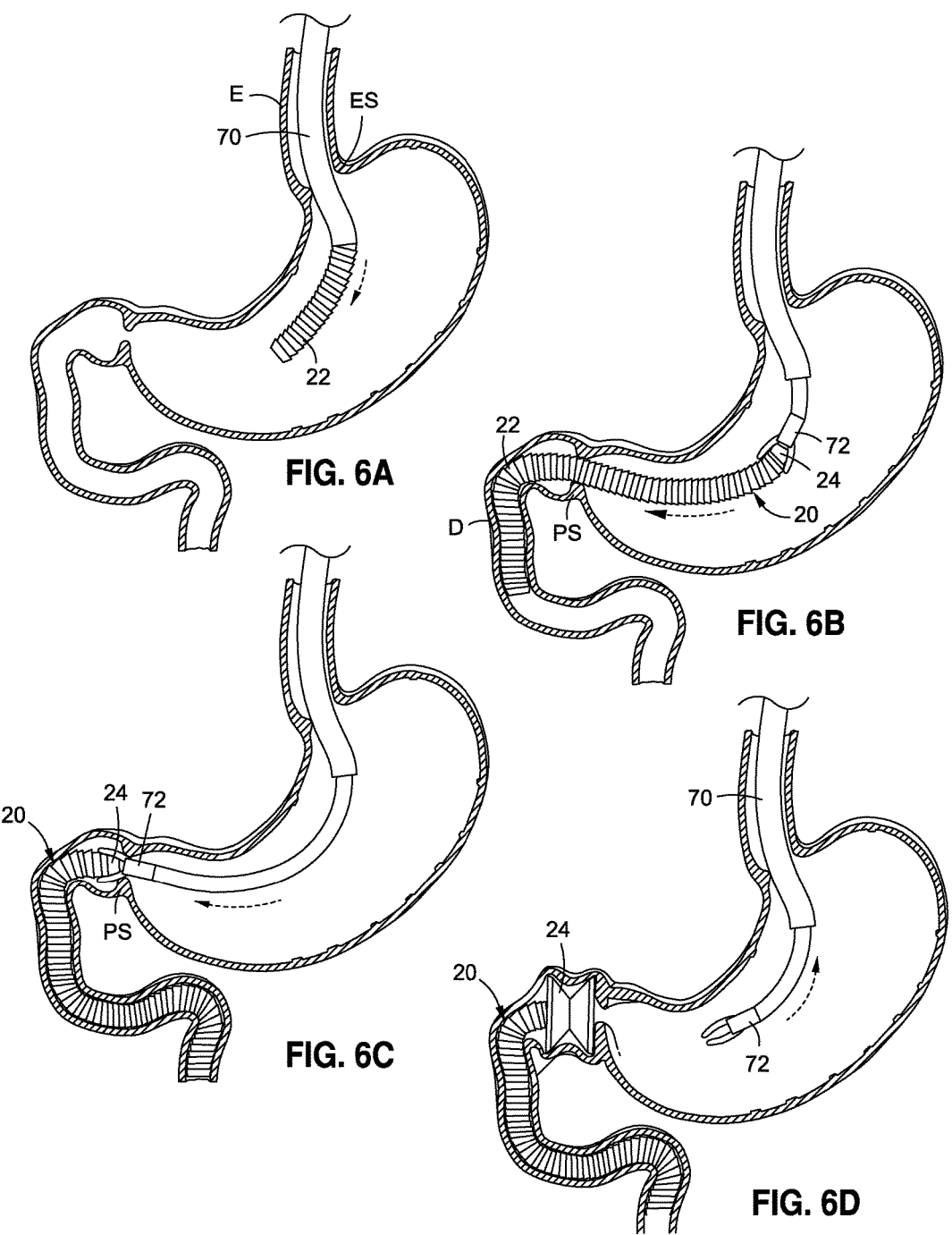
FIGS. 6A-6D show the collapsed/compressed intragastric obesity treatment implant within a flexible delivery tube inserted down the esophagus and expelled for subsequent advancement through the pyloric sphincter into an implant position.

FIGS. 6A-6D show an alternative delivery of the implant 20 using a flexible delivery tube 70 inserted down the esophagus E. In FIG. 6A the delivery tube 70 has entered the stomach through the esophageal sphincter ES and the distal end of the duodenal sleeve 22 projects from its distal end. As will be seen, a pusher or grasper may be used to advance the implant 20 relative to the delivery tube 70. Typically, an endoscope passed parallel with or through the delivery tube 70 is used to visualize the locations of the delivery tube and implant, but will not be shown for clarity.

FIG. 6B illustrates advancement of the distal end of the distal portion of the duodenal sleeve 22 through the pyloric sphincter PS and into the duodenum D (again, typically with the aid of an endoscope). It should be noted that the implant 20 is shown in an expanded state in this sequence, but essentially the same steps could be used to deliver a collapsed/compressed implant. A distal end of a grasper 72 is seen holding the anchor 24 of the implant 20, which is one way to push the device through the tube 70.

FIG. 6C then shows the implant 20 fully advanced to its implant position. The grasper 72 remains holding and compressing the anchor 24 so that it may fit through the pyloric sphincter PS. Again, an alternative method is a jacket that maintains constriction around the anchor 24.

Finally, FIG. 6D shows the implant 20 fully deployed, with the anchor 24 expanded outward into contact with the duodenal bulb, as in FIGS. 1 and 2. The grasper 72 retracts back up the delivery tube 70, and the tube is then withdrawn to complete the implant procedure.

A removal procedure consists of placing a long overtube down the esophagus E such that the tube ends reach from the mouth and into the stomach S. Next, a long-handled grasping tool or specially made removal device should be inserted down the overtube. By operating the grasper to grasp onto the inside of the anchoring portion 24, the implant 20 can be gently pulled, so as to guide it back through the pylorus and into the overtube. Pulling on the implant 20 continues until the grasped anchor end 24, along with the entire trailing sleeve 22 has been removed through the mouth. It is anticipated that this removal procedure will cause only slight throat irritation from the overtube, but will not induce excessive trauma.

The intragastric obesity treatment implant 20 is intended to be a single use implant placed in the stomach transorally without invasive surgery, and recovery time is believed to be minimal. The device may desirably be left in place one year or longer, which is somewhat material-dependent in the acidic stomach environment.

Figure 7:
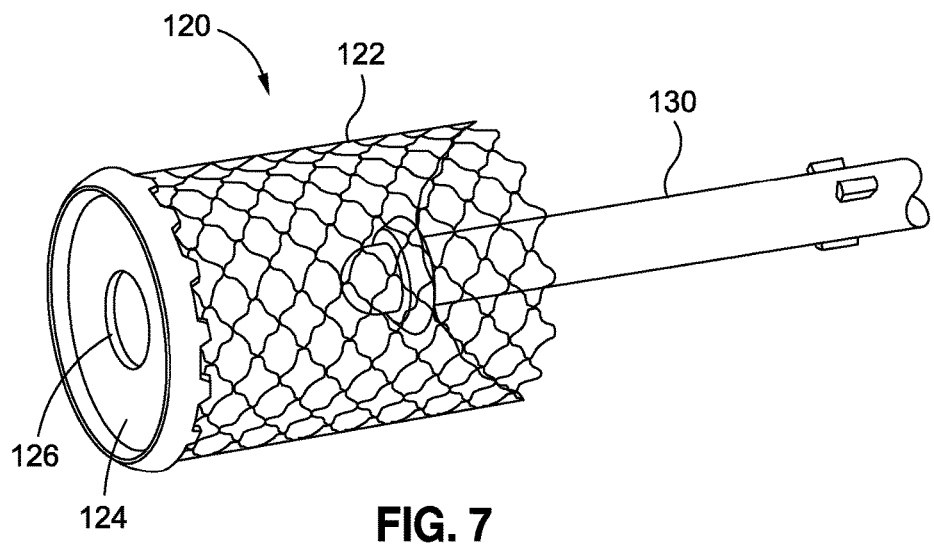
FIGS. 7 and 8 are perspective views of an intragastric obesity treatment device that can be used to form an artificial stoma.
Figure 8:
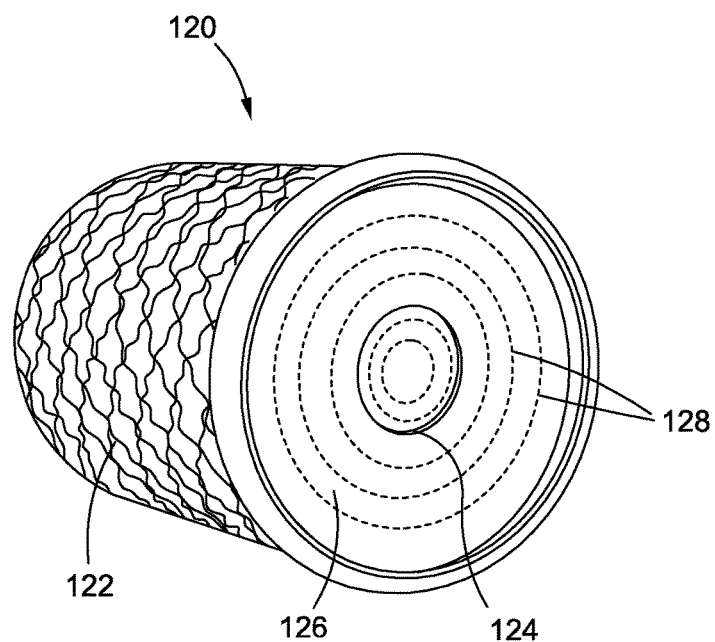

Another device 120 that regulates the amount of food allowed to pass from the stomach into the duodenum is seen in FIGS. 7 and 8 and comprises an artificial stoma. The device includes a tubular stent 122 for anchoring in a passage and a stoma diaphragm 124 that extends perpendicularly over one end of the stent. The diaphragm 124 defines a stoma opening 126 and may be provided with fold lines such as seen at 128 in FIG. 8 for easy collapse.

The device 120 is designed to be placed inside the stomach, just above the pylorus. The stent 122 contacts the stomach cavity walls and the stoma diaphragm 124 acts to regulate the amount of food allowed to pass from the stomach into the duodenum, thus slowing stomach emptying. The device 120 also exerts some pressure upon the lower part of the stomach.

With the device 120 of FIGS. 7 and 8, hole-size restriction is believed to slow emptying of partially digested food from one organ to the next. The placement will not have as great a potential for causing GERD (Gastro Esophageal Reflux Disease) since stomach installation is below the esophageal sphincter (within the lower stomach), unlike certain devices configured for placement at the esophageal sphincter.

The outside diameter of the stoma is constructed in one size. Several fixed hole sizes may be made available to allow various restricted amounts of food to pass into the stomach. For instance, three fixed OD sizes are believed sufficient designed to fit within lower esophagus of most patients. Small (12 mm), medium (15 mm), and large (18 mm) stoma openings are provided depending on the patient's needs. Additionally, a single, optimized OD size could be made, that would universally suit all patients.

A temporary, removable surgical obturator 130 (FIG. 7) is used to hold the stent in a compressed state, so it will fit comfortably down the esophagus. Anchoring is achieved within the pyloric sphincter by self-expansion.

Figure 9:
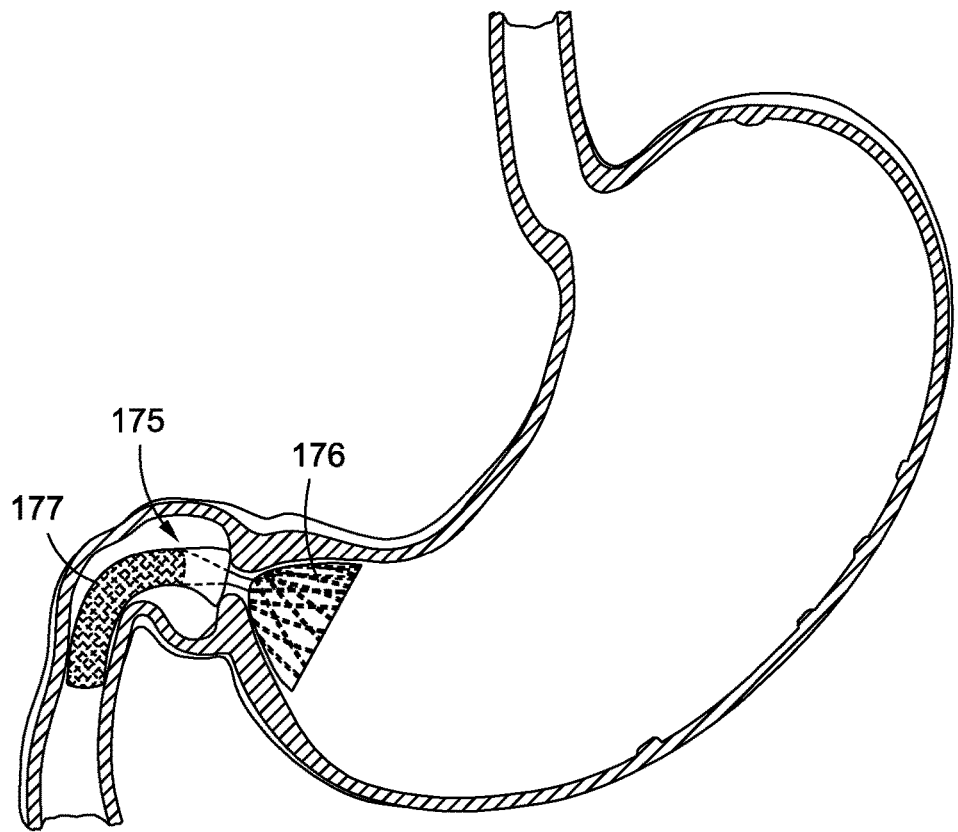
FIG. 9 illustrates an expandable umbrella having a duodenal anchor positioned in the stomach.
Figure 9A:
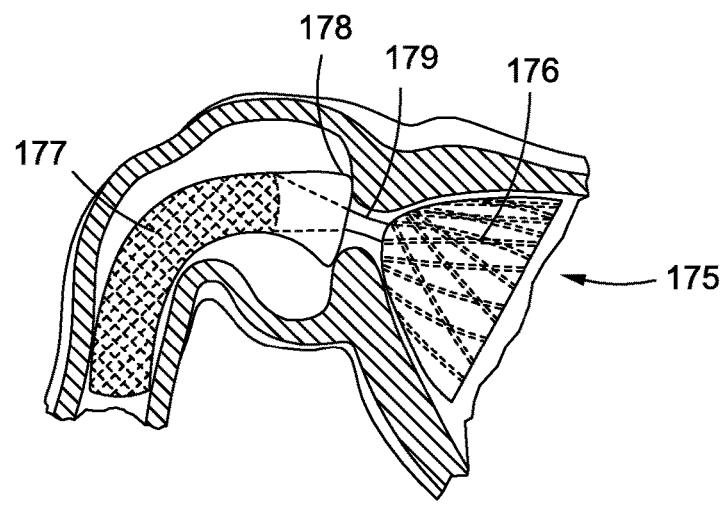
FIG. 9A is an enlarged view thereof.

FIG. 9 shows a further intragastric obesity treatment device 175 implanted in the stomach having an expandable umbrella-shaped conical anchor 176 with a duodenal anchor 177. The device 175 is designed to span the pyloric sphincter, and is shown in more detail in FIG. 9A. The device 175 anchors on the stomach side of the pyloric sphincter with the umbrella-shaped anchor 176, which desirably comprises an expandable stent-like device. The anchor 176 incorporates features (e.g. metal/plastic mesh) that will give it structure which will help prevent its migration through the pylorus. The distal side consists of a sleeve-like anchor 177 which incorporates features on its outer surface, such as shoulder 178, which prevent migration back into the stomach. An internal passage along the entire device, which includes a narrow neck portion 179, allows food to pass therethrough, although with some restriction which delays gastric emptying. Narrowing of the neck portion 179, and possibly a collapsible construction, provides little resistance to closing action of the pyloric sphincter. At the terminal end of the device, a fixed size stoma (not shown) may be provided which further delays gastric emptying. The duodenal anchoring sleeve 177 also provides a barrier across which there can be no nutrient transfer to the body. The main mode of action of this device is malabsorptive (limits nutrient transfer to body through duodenum). A second mechanism is this device's potential ability to delay gastric emptying, thereby facilitating a rapid achievement of satiety as the stomach fills (but does not empty as fast as normal) and also prolonging the feeling of satiety once reached.

Figure 10:
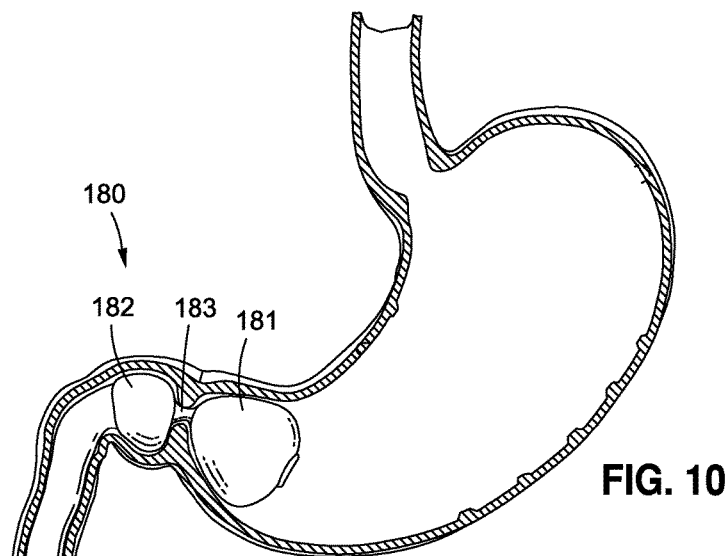
FIGS. 10 and 10A show an intragastric obesity treatment device implanted in the stomach with a flow channel spanning the pyloric sphincter and a duodenal sleeve.
Figure 10A:
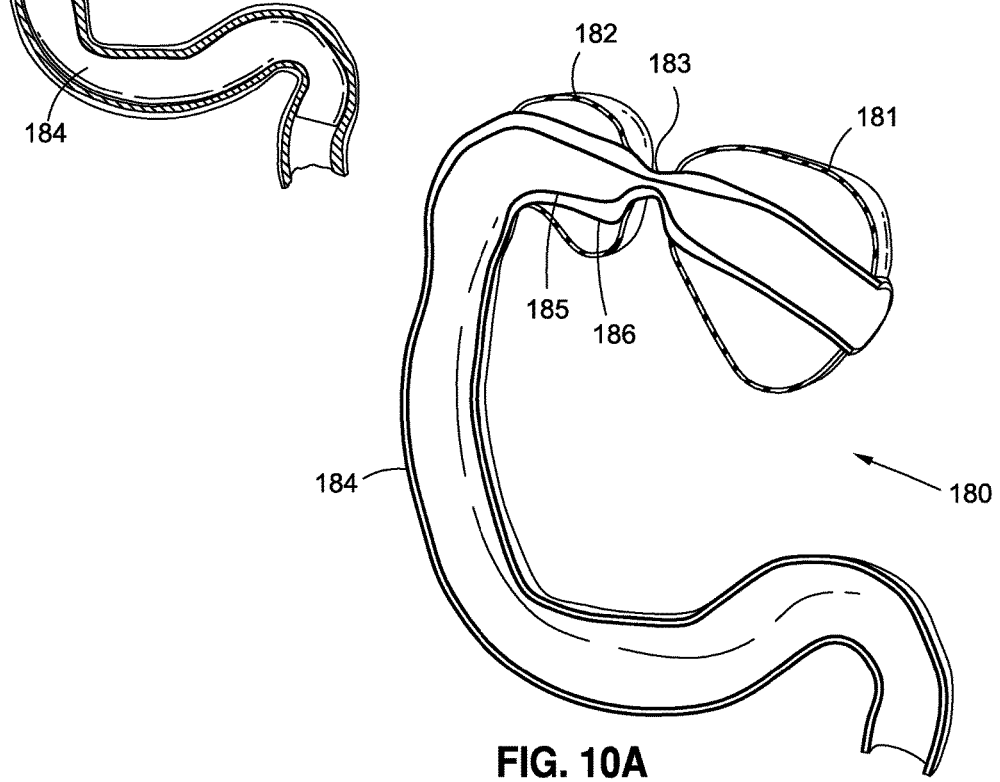

FIGS. 10 and 10A show an intragastric obesity treatment device 180 implanted in the stomach that shares some similarities with the device 175 of FIG. 9 in that it creates a flow channel spanning the pyloric sphincter and has a duodenal sleeve. More particularly, the device 180 provides an inflatable anchor 181 that sits against the pylorus and prevents the device from passing entirely through the pyloric sphincter. A second balloon 182 somewhat smaller than the first sits just inside the duodenum. The balloons 181, 182 seat on both sides of the pylorus and serve as anti-migration features so the device 180 cannot migrate down through the intestines or back into the stomach. The balloons 181, 182 include through bores and narrow passageway 183 extends between them at the pyloric sphincter. Since the material is soft and thin-walled material, the pyloric sphincter is able to close over the passageway 183, allowing it to "seal" shut.

In addition to the two balloons, an inflatable sleeve 184 fixed at its proximal end to the second balloon 182 extends down the duodenum. This is a malabsorptive sleeve that prevents nutrient absorption in the jejunum. The sleeve 184 is inflatable which provides means for positioning and anchoring. More particularly, the sleeve 184 consists of dual walls 185, 186 that form an inflatable bladder along the shaft of the sleeve, so there are inner and outer sleeve walls, closed at both ends, while the sleeve inner lumen remains hollow and open. Inflation of the sleeve 184 is an anti-rotational feature within the jejunum and also helps prevent "bunching-up" and twisting.

The three inflatable members of the balloon 181, 182 and sleeve 184 could be connected or separate (not air or fluid communicating). The entire device can be inflated with air or liquid. The sleeve 184 passes through the dual balloons 181, 182 and into the stomach, so food is allowed to flow freely from the stomach, directly to the lower intestine, where nutrient absorption is less. On that basis, weight loss is achieved.

As mentioned before, a number of independent characteristics disclosed for the various embodiments included herein may be transferred to other embodiments. For example, several versions of the intragastric obesity treatment device included a threaded bore to mate with a threaded end of an obturator for delivering and removing the device to and from the stomach (e.g., FIG. 9). Likewise, a similar arrangement can also be included on embodiments where it is not specifically shown.

Figure 11:
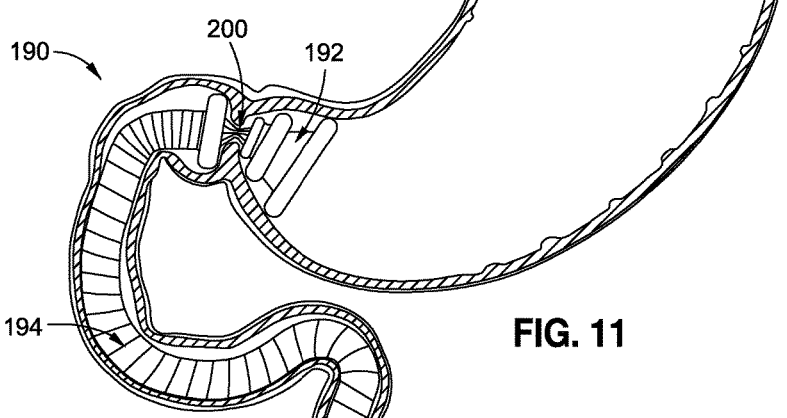

FIG. 11 shows another intragastric device 190 implanted in the stomach with a conical anchor 192 securing an upper end of a ribbed duodenal sleeve 194 that lines the upper duodenal wall. The duodenal sleeve 194 partially prevents nutrient absorption by inhibiting or delaying the point at which chyme from the stomach contacts the mucous membranes of the intestine.

Figure 12A:
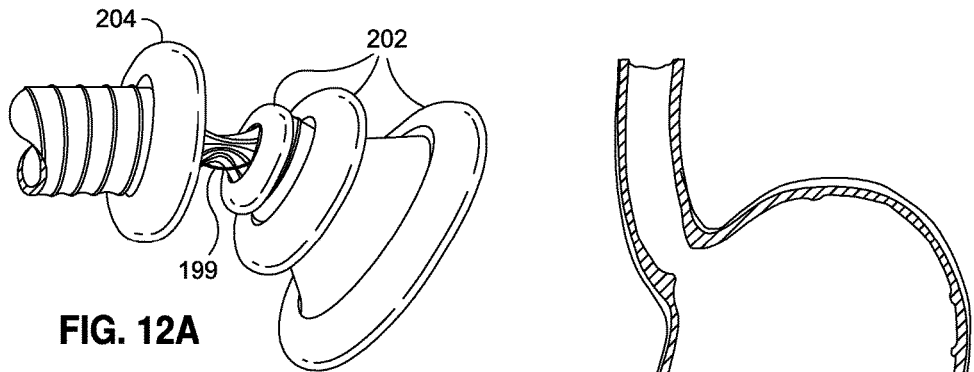
FIGS. 11 and 12A-12C illustrate another intragastric device implanted in the stomach with a flow channel spanning the pyloric sphincter and a ribbed duodenal sleeve.
Figures 12B, 12C:
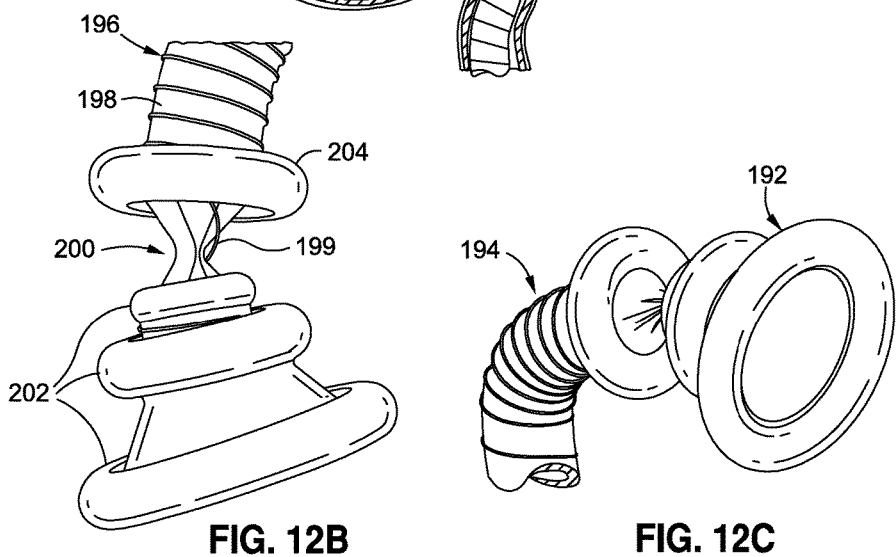

As seen best in FIGS. 12A-12C, the sleeve 194 comprises a spring-like spiral wire 196 of coated metal or other stiff material embedded in a thin flexible sleeve wall 198. The spiral wire 196 therefore renders the sleeve wall 198 more robust and less prone to kinking Specifically, the spiral loops or windings of the wire 196 provide circumferential support, so the entire sleeve 194 is less likely to collapse or twist. A proximal end of the sleeve 194 passes through the pyloric sphincter in a necked-down region 200 and connects to the conical anchor 192. To avoid twisting or closing-off of the necked-down region 200, an integral loop 199 of the spiral wire 196 passes through the sphincter along with the sleeve wall 198, and is secured to the conical anchor 192, such as by being embedded therein. The necked-down region 200 preferably comprises a creased structure having a series of longitudinal folds that enable the region to collapse. The pyloric sphincter may move in and out which causes the lumen within the necked-down region 200 to flex, though the wire loop 199 maintains a minimum orifice patency and prevents total collapse.

The conical anchor 192 features a number of co-linear circular O-rings 202 in graduated sizes that provide good hoop strength to the anchor and prevent migration of the anchor through the pyloric sphincter. To prevent outward migration of the device back into the stomach, a further circular O-ring 204 is integrally formed on the proximal end of the ribbed sleeve 194. In a preferred embodiment, the material of the device 190 other than possibly the spiral wire 196 is a flexible polymer such as silicone having sufficient elasticity such that the O-rings 202, 204 prevent passage through the pyloric sphincter from either side. The spiral wire 196 may be a sufficiently flexible metal, such as Nitinol, or a polymer more rigid than the sleeve wall 198.

Implantation of the intragastric device 190 involves collapsing the device so it can be introduced through an elongated flexible transoral delivery tube. The duodenal sleeve 194 may be collapsed by virtue of the flexibility of the spiral wire 196. Similarly, the device can be grasped and pulled to collapse within a similar tube for removal.

Figure 13:
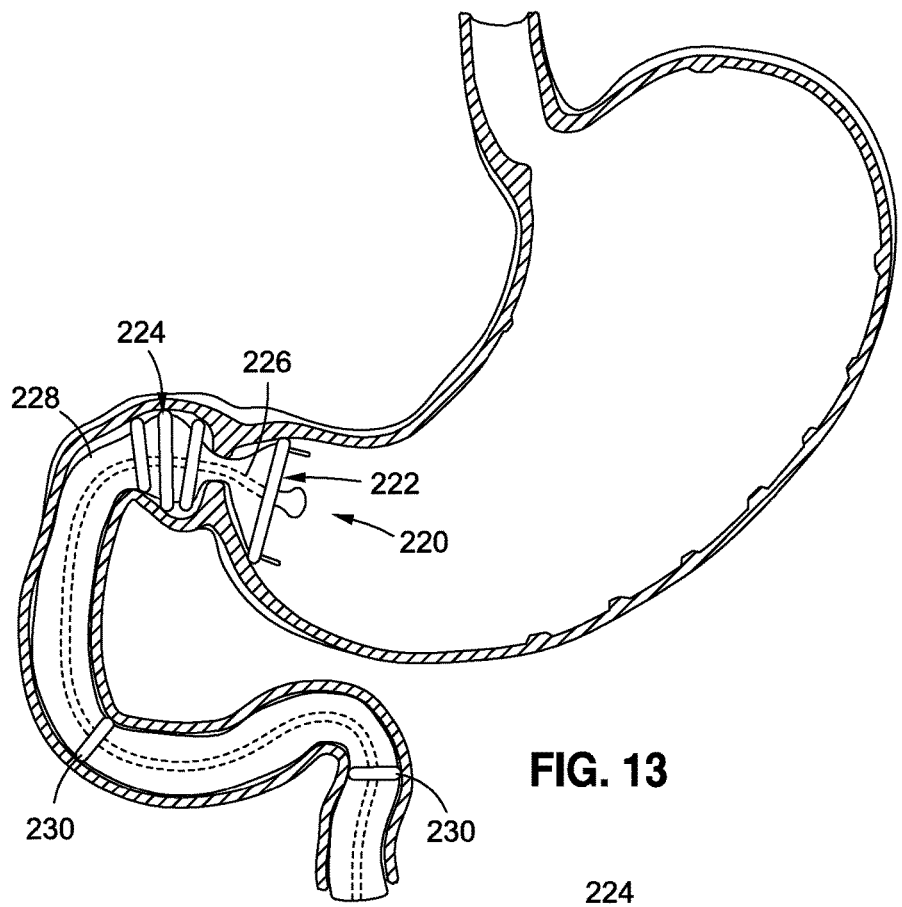

FIG. 13 illustrates an intragastric device 220 implanted in the stomach that spans the pyloric sphincter and extends into the duodenum. The device 220 includes a stomach anchoring member 222, a duodenal anchoring member 224, flexible cords 226 that extend the length of the device, and a tubular duodenal sleeve 228. As with the earlier embodiments, the intragastric device 220 is non-tissue-piercing and anchors across the pyloric sphincter using flexible, resilient and soft structures that expand outward into contact with the surrounding cavity or passage.

The duodenal sleeve 228 extends the full length of the device with a proximal end extending to the stomach anchoring member 222 on the stomach side of the pyloric sphincter and a distal end preferably extending into the jejunum J (see FIG. 1). As such, the duodenal sleeve 228 extends through the pyloric sphincter. Because of its extremely flexible nature, the duodenal sleeve 228 provides a compressible channel that flexes with the pyloric sphincter. As usual, the duodenal sleeve 228 promotes malabsorption and restriction of the size of the flow passage through the duodenum and jejunum. Although not shown, the sleeve 228 may further include anti-migration ribs as described above with respect to the sleeve 22 in the embodiment of FIG. 1. A plurality of anti-migration/anti-kinking rings 230 may be provided spaced along the length of the duodenal sleeve 228, preferably structurally connected to the flexible cords 226. Radiopaque markers provided in the rings 230 will be useful for ensuring proper deployment of the sleeve 258. In the illustrated embodiment, there are two rings 230 spaced approximately halfway down and toward the distal end of the sleeve 258. The flexible cords 226 tie together the entire structure, and provide anti-migration/anti-kinking characteristics also. The cords 226 are desirably formed from strips of silicone or other elastomers. In the illustrated embodiment, there are two such cords 226 diametrically opposed across the device and extending in parallel the full length thereof, though more than two may be provided.

Figure 14:
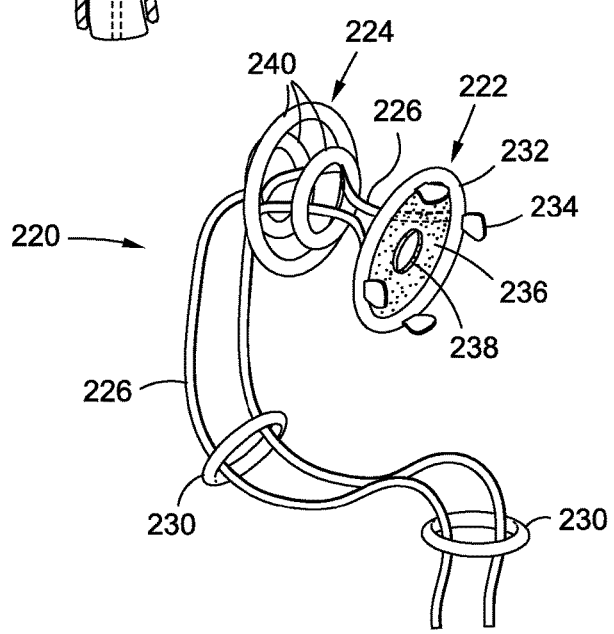
FIG. 14 shows the device isolated and with the duodenal sleeve removed for clarity.

With reference to FIG. 14, the device 220 is shown without the duodenal sleeve 228 for clarity. The stomach anchoring member 222 comprises a resilient outer ring 232 having a plurality of grasping tabs 234 projecting in a proximal direction. The grasping tabs 234 aid in removal of the device by permitting the device 220 to be easily grasped by forceps, for example. To facilitate removal, the tabs 234 may be provided with radiopaque markers. An annular flexible membrane 236 having a central through hole 238 spans the orifice defined by the outer ring 232. The through hole 238 presents an artificial stoma to help restrict the rate that food can pass from the stomach into the duodenum. Due to the high elasticity of the flexible membrane 236, the through hole 238 can widen under sufficient pressure, such as when the stomach is very full, though this is desirably just a safety valve, with normal food intake not overly distorting the flexible membrane. In normal use, the opening 238 defines the size of the orifice through which food can pass into the duodenum. Of course, the diameter of the opening 238 can be varied for different patients.

The duodenal anchoring member 224 comprises a series of resilient rings 240 that are desirably sized to match the contours of the duodenal bulb area, just distal to the pyloric sphincter. In particular, as seen in FIG. 13, two smaller diameter rings flank a larger central ring to define a bulge and match the bulb area. As with the outer ring 232 of the stomach anchoring member 222, the resilient rings 240 of the duodenal anchoring member 224 preferably comprise an elastomer, such as silicone, and resemble O-rings. If greater anchoring force is deemed necessary, the rings 232, 240 may be formed with metallic cores embedded within a suitable soft coating. One example is a Nitinol ring embedded within a silicone outer covering.

Figure 15:
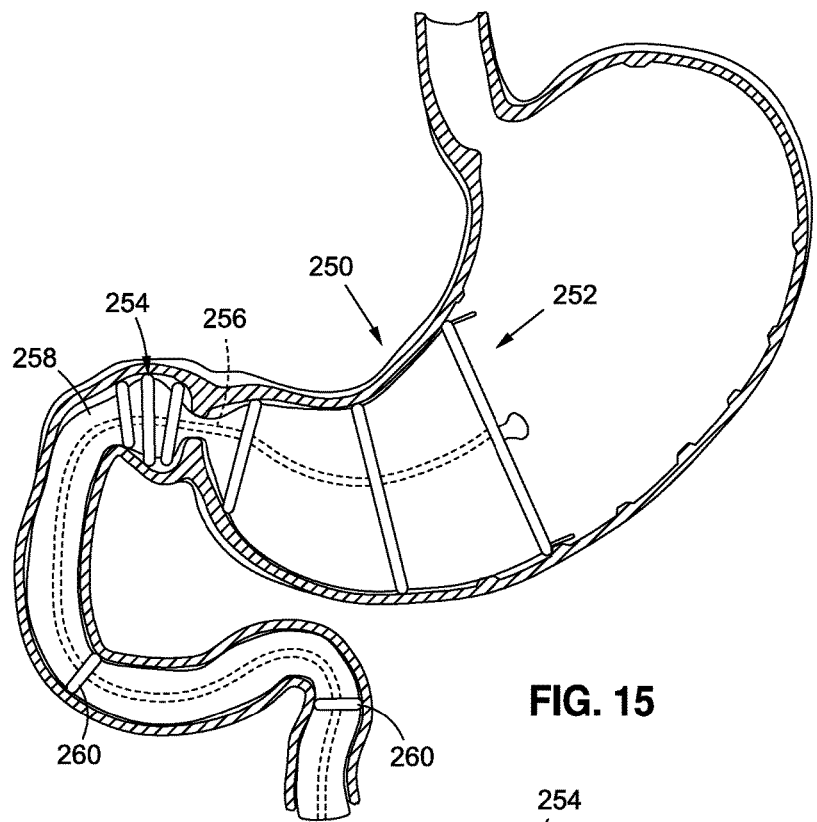
FIG. 15 shows a still further intragastric device in the stomach similar to that shown in FIG. 13, but having an enlarged funnel-like anchor in the lower stomach.
Figure 16:
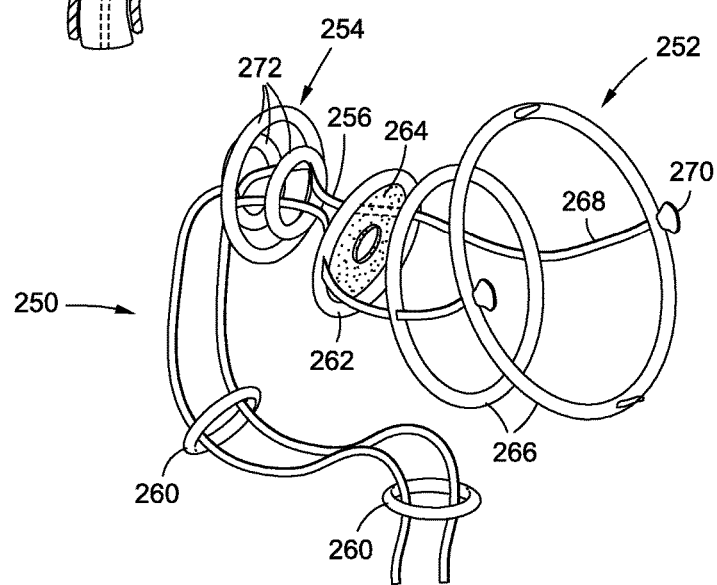
FIG. 16 shows the device isolated with the duodenal sleeve removed for clarity.

FIG. 15 illustrates a further intragastric device 250 that spans the pyloric sphincter and extends into the duodenum. As with the intragastric device 220 described above, the device 250 includes a stomach anchoring member 252, a duodenal anchoring member 254, a pair of flexible cords 256 that extend the length of the device, and a duodenal sleeve 258. Again, a plurality of anti-migration/anti-kinking rings 250 are desirably spaced along the length of the duodenal sleeve 258, preferably structurally connected to the flexible cords 256. The flexible cords 256 tie together the entire structure, and also provide anti-migration/anti-kinking characteristics. In contrast to the earlier embodiment, the gastric device 250 has an enlarged funnel-like stomach anchoring member 252. In a preferred embodiment, the duodenal sleeve 258 extends the full length of the device, all the way into the stomach along the funnel-like anchoring member 252.

The stomach anchoring member 252 comprises a series of resilient rings that define its shape. A resilient outer ring 262 having a flexible annular membrane 264 therein resides just inside the stomach adjacent to the pyloric sphincter. The outer ring 262 and annular membrane 264 function the same as the same elements in the embodiment of FIGS. 13-14, and specifically regulate the rate of flow from the stomach into the duodenal sleeve 258. Progressively larger resilient rings 266 define the funnel shape of the remainder of the anchoring member 252. The funnel shape thus created conforms to the lower end of the stomach cavity, potentially stimulating the antrum in the process which helps induce satiety. Proximal portions 268 of the flexible cords 256 continue to the proximal most resilient ring 266. Grasping tabs 270 are desirably provided on the proximal end of the device 250, and preferably comprise proximal ends of the extension cords 260. The cords 260 thus provide a skeleton of sorts for the device 250 which helps facilitate removal thereof.

The duodenal anchoring member 254 is preferably formed the same as that described above, with a series of resilient rings 272 that conform to the upper bulb area of the duodenum. Once implanted, the large sizes of both the stomach anchoring member 252 and duodenal anchoring member 254 are sufficient to hold the entire device on both sides of the pyloric sphincter without the need for barbs or other tissue-piercing devices.

It should also be stated that any of the embodiments described herein may utilize materials that improve the efficacy of the device. For example, a number of elastomeric materials may be used including, but not limited to, rubbers, fluorosilicones, fluoroelastomers, thermoplastic elastomers, or any combinations thereof. The materials are desirably selected so as to increase the durability of the device and facilitate implantation of at least six months, and preferably more than 1 year.

Material selection may also improve the safety of the device. Some of the materials suggested herein, for example, may allow for a thinner wall thickness and have a lower coefficient of friction than the current device which may aid in the natural passage of the balloon through the GI tract should the device spontaneously deflate.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:

Silicone materials used include 3206 silicone for any shells, inflatable structures, or otherwise flexible hollow structures. Any fill valves will be made from 4850 silicone with 6% $BaSO_4$. Tubular structures or other flexible conduits will be made from silicone rubber as defined by the Food and Drug Administration (FDA) in the Code of Federal Regulations (CFR) Title 21 Section 177.2600.

Purposes:

the devices are for human implant, the devices are intended to occupy gastric space while also applying intermittent pressure to various and continually changing areas of the stomach;

the devices are intended to stimulate feelings of satiety, thereby functioning as a treatment for obesity.

General Implant Procedures:

The device is intended to be implanted transorally via endoscope into the corpus of the stomach.

Implantation of the medical devices will occur via endoscopy.

Nasal/Respiratory administration of oxygen and isoflurane to be used during surgical procedures to maintain anesthesia as necessary.

One exemplary implant procedure is listed below.

a) Perform preliminary endoscopy on the patient to examine the GI tract and determine if there are any anatomical anomalies which may affect the procedure and/or outcome of the study.

b) Insert an introducer into the over-tube.

c) Insert a gastroscope through the introducer inlet until the flexible portion of the gastroscope is fully exited the distal end of the introducer.

d) Leading under endoscopic vision, gently navigate the gastroscope, followed by the introducer/over-tube, into the stomach.

e) Remove gastroscope and introducer while keeping the over-tube in place.

f) OPTIONAL: Place the insufflation cap on the over-tubes inlet, insert the gastroscope, and navigate back to the stomach cavity.

g) OPTIONAL: Insufflate the stomach with air/inert gas to provide greater endoscopic visual working volume.

h) Collapse the gastric implant and insert the lubricated implant into the over-tube, with inflation catheter following if required.

i) Under endoscopic vision, push the gastric implant down the over-tube with gastroscope until visual confirmation of deployment of the device into the stomach can be determined.

j) Remove the guide-wire from the inflation catheter is used.

k) If inflated: Inflate the implant using a standard BioEnterics Intragastric Balloon System ("BIB System") Fill kit.

l) Using 50-60 cc increments, inflate the volume to the desired fill volume.

m) Remove the inflation catheter via over-tube.

n) Inspect the gastric implant under endoscopic vision for valve leakage, and any other potential anomalies. Record all observations.

o) Remove the gastroscope from over-tube.

p) Remove the over-tube from the patient.

End Point Criteria:

Weight Loss

Comprehensive Metabolic Panel (CMP)

HbA1C

Lipid Panel

Tissue Samples/Response

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention(especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of or" consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A transorally inserted, intragastric device for a treatment of obesity, comprising:
    a sleeve for placement in a duodenum having a tubular body with proximal and distal ends and an inner lumen; and
    a radially collapsible anchor surrounding the proximal end of the tubular body, the anchor having an expanded state that can act to prevent passage of the device through a pyloric sphincter, the anchor including tubular a proximal conical flange and a distal conical flange concentrically-disposed around the tubular body and angled away from one another so as to impede movement of the anchor within the duodenum in both a proximal direction and in a distal direction, wherein the proximal conical flange forms an intake funnel having a proximal opening, the intake funnel leading into the inner lumen of the sleeve, the inner lumen being smaller than the proximal opening of the intake funnel, wherein the device is formed of a material that will resist structural degradation over a period of at least six monthly within a gastrointestinal tract.

2. The device of claim 1, wherein the sleeve includes exterior ribs to resist movement within the duodenum in one direction.

3. The device of claim 2, wherein the exterior ribs on the sleeve are conical and extend the length of the sleeve and angle in the proximal direction to resist movement within the duodenum in the proximal direction.

4. The device of claim 3, wherein the sleeve is axially collapsible/expandable and the conical ribs are shaped to nest within one another for axial collapse of the sleeve.

5. The device of claim 1, wherein the anchor surrounding the proximal end of the tubular body has no metal component.

6. The device of claim 1, wherein the proximal flange tapers from a wide base at a proximal end and to a narrow circular edge at a distal end and wherein the distal flange tapers from a wide base at a distal end to a narrow circular edge at a proximal end.

7. The device of claim 1, wherein a smallest diameter of the intake funnel coincides with a diameter of the lumen.

8. The device of claim 7, wherein the smallest diameter of the intake funnel and the diameter of the lumen are sized to reduce a flow rate exiting the stomach through the pyloric sphincter.

* * * * *